United States Patent
Stevenson et al.

(10) Patent No.: US 7,176,252 B2
(45) Date of Patent: Feb. 13, 2007

(54) SOLID MELT BLENDED PHOSPHITE COMPOSITES

(75) Inventors: Donald R. Stevenson, Dover, OH (US); Satyan Kodali, Dover, OH (US); Carroll W. Larke, Zoar, OH (US)

(73) Assignee: Dover Chemical Corporation, Dover, OH (US)

( * ) Notice: Subject to any disclaimer, the term of this patent is extended or adjusted under 35 U.S.C. 154(b) by 17 days.

(21) Appl. No.: 10/778,492

(22) Filed: Feb. 13, 2004

(65) Prior Publication Data

US 2004/0164279 A1      Aug. 26, 2004

Related U.S. Application Data

(63) Continuation-in-part of application No. 09/363,598, filed on Jul. 29, 1999, now abandoned.

(51) Int. Cl.
*C08K 5/527* (2006.01)
*C09K 15/32* (2006.01)

(52) U.S. Cl. .................. 524/128; 524/151; 524/153; 252/400.24

(58) Field of Classification Search ........... 252/400.24; 524/128, 151, 153
See application file for complete search history.

(56) References Cited

U.S. PATENT DOCUMENTS

| | | | |
|---|---|---|---|
| 4,957,956 A | 9/1990 | Neri et al. | |
| 5,438,086 A | 8/1995 | Stevenson et al. | |
| 5,844,042 A | 12/1998 | Neri et al. | |
| 6,075,158 A | 6/2000 | Hill | |

FOREIGN PATENT DOCUMENTS

EP      03 05371      12/2003

*Primary Examiner*—Peter Szekely
(74) *Attorney, Agent, or Firm*—Louis F. Wagner; Buckingham, Doolittle & Burroughs, LLP

(57) ABSTRACT

A solid phosphite composite, having at least a portion in amorphous form, which includes at least one, preferably two or more phosphite antioxidants or alternatively at least one phosphite and at least one other polymer additive. The phosphites, at least one of which can initially be a liquid, are generally uniformly distributed since they are melt blended. A desired class of phosphites are the bis(arylalkylphenyl) pentaerythritol diphosphites, at least a portion of which is in amorphous form.

52 Claims, No Drawings

SOLID MELT BLENDED PHOSPHITE COMPOSITES

This application is a continuation-in part of application Ser. No 09/363,598, filed Jul. 29, 1999, now abandoned.

TECHNICAL FIELD

This invention relates to the preparation and use of solid melt blended composites derived from solid, high-melting crystalline phosphites at least a portion of which has been modified to lower-melting amorphous phosphites, with one or more polymer additives, including additional phosphites, in liquid or solid form, to give a solid blend having superior performance in the stabilization of polymers. More specifically, the present invention relates to solid phosphite composites at least a portion of which contains amorphous bis(arylalkylphenyl)pentaerythritol diphosphites, which have high melting points in the crystalline form, and show unusual melt behavior (initially cooling rapidly from the melt to a non-crystalline solid glass, which upon heating gives first a clear melt, then crystallizes to give a high-melting solid) with lower-melting or liquid phosphites or other polymer additives. These solid melt-blended composites having a percentage of amorphous component, are useful as stabilizers for several polymers, e.g., polypropylene, polyethylene, polyesters, polycarbonates, polyamides, polyurethanes, polysulfones, polyimides, polyphenylene ethers, styrenic polymers, acrylic polymers, polyacetals, halide-containing polymers and copolymers thereof in that they are better distributed within organic polymers which are processed at relatively low temperatures.

BACKGROUND OF THE INVENTION

Heretofore, phosphites have been utilized as antioxidants for various polymers, both alone and in blends with other stabilizers. There are two basic types of antioxidants, primary and secondary. Primary antioxidants intercept and stabilize free radicals by donating active hydrogen atoms, interrupting the free-radical chain oxidation. Hindered phenols and aromatic amines represent the two main types of primary antioxidants. Secondary antioxidants prevent formation of additional free radicals by decomposing the unstable hydroperoxides into a stable product, thus removing a source of free radical formation which accelerates the oxidation. Phosphites and thioesters are secondary antioxidants that function by decomposing hydroperoxides, thus preventing free-radical formation. Secondary antioxidants are often used along with primary antioxidants, but can be used alone, especially if they contain a hindered phenolic group within their structure. Together they decrease the discoloration of the polymer and may also regenerate the primary antioxidant.

In U.S. Pat. No. 4,187,212, Zinke et al. disclose that a mixture of aryl-containing phosphites and ortho-substituted phenols in polyolefins exhibits a particularly good stabilizing effect. This particular degree of effectiveness is reflected especially in the excellent absence of discoloration in the resulting polymers. In this case, the phosphites exemplified are tris-aryl phosphites, which are known from the prior art to have good hydrolytic stability. The stabilizer mixtures, in this case, are physical mixtures of powders and are incorporated into the polymer by powder blending and subsequent processing in a kneading machine, mixing rolls, or extruder.

As set forth in U.S. Pat. No. 4,957,956, a solid stabilizer composition for organic polymers is formed by a mixture of a solid, continuous phase of a phenolic antioxidant, namely tetrakis[3-(3,5-di-tert-butyl4-hydroxyphenyl)propionyloxymethyl] methane and the dispersed phase is constituted by either an amorphous or crystalline organic phosphite in the form of particles with a particle size from 10 um to 2 mm, with the weight ratio of the continuous phase to the dispersed phase within the range of 9:1 to 1:9.

The above patent pointed out that in the use of mixtures of sterically hindered phenols and organic phosphites in the stabilization of organic polymers, difficulties exist in accomplishing complete homogenization between the two stabilizers, and between these and the organic polymer. With blends of solid powdered stabilizers, intimate mixing is often not achieved, and often the stabilizing effect of the stabilizers shown does not reach the maximum possible level. Often this fact, combined with the phenomenon of hydrolysis of the phosphite is subject to, does not allow as high a stabilizing effect as desired. When certain organic phosphites are introduced to the polymer as a dispersed (solid particulate) phase in a continuous amorphous phase of tetrakis[3-(3,5-di-tert-butyl-4-hydroxyphenyl)propionyloxymethyl] methane, a few of said phosphites are endowed with exceptionally high characteristics of resistance to hydrolysis.

In the case of U.S. Pat. No. 4,957,956, the stabilizer composites are produced by mixing the powders of the organic phosphite and the tetrakis [3-(3,5-di-tert-butyl-4-hydroxyphenyl)propionyloxymethyl] methane, then under nitrogen or another inert gas, the mass is raised to a temperature which is typically on the order of 160° C. to 170° C. The mass is homogenized and is then submitted to a sudden cooling down to temperature values equal to room temperature (20° C.–25° C.).

U.S. Pat. No. 5,155,153 describes a stabilizer composite for organic polymers containing a three-component mixture of a sterically hindered phenol, a triaryl phosphite, and a dialkylthiodipropionate. Stabilized compositions are made by simple addition of the three components to the polymer.

U.S. Pat. No. 5,844,042 relates to a process for obtaining granular forms from mixtures of powders of two or more additives for organic polymers, which comprises extruding the additive mixture at a temperature between the melting point of the component with the lowest melting point and about 140° C., with the condition that, when the mixture consists of two additives, these are not tetrakis[3-(3,5-di-tert-butyl-4-hydroxyphenyl)propionyloxymethyl] methane, either in a crystalline or amorphous phase, and an antiacid. Other attempts to produce effective stabilizer blends for the stabilization of organic polymers are described, e.g., extruding a mixture of at least two components below the melting point of the highest melting component and above the melting point of the lowest melting component.

In U.S. Pat. No. 5,845,656, a mixture of stabilizers is made in a pelletized form from a homogenous mixture of at least one stabilizer and an agent which will prevent melting of the stabilizer. The stabilizers are antioxidants such as organic phosphites and hindered phenols, hindered amines, U. V. light stabilizers, or combinations thereof. If the mixture is permitted to melt, pellets of the stabilizer mixture are not able to be produced by the method of this patent.

SUMMARY OF THE INVENTION

It is an aspect of the present invention to provide a solid composite containing two or more phosphites, one of which has at least a portion of which is in the amorphous form, with or without other polymer additives.

Another aspect of the present invention is to provide a phosphite composite of the above having two or more phosphites randomly or uniformly distributed therein and having at least one phosphite in the composite at least partially present in the amorphous form with a melting point from about 50° C. to about 65° C.

Yet another aspect of the invention is to provide a solid phosphite composite as above, which is formed by heating and mixing at least two phosphite compounds above their melting points and rapidly cooling the same to produce a solid phosphite composite and wherein the composite desirably contains bis(arylalkylphenyl)pentaerythritol diphosphite, at least a portion of which is present in the amorphous form.

As still another aspect of the present invention is to provide a solid phosphite composite, wherein one of the phosphite components can initially be a liquid.

An alternative aspect of the present invention is to provide a solid composition containing one or more phosphites and one or more polymer additives wherein the polymer additive can be liquid or solid.

It is yet another aspect of the present invention to provide a solid phosphite composite containing at least one phosphite at least a portion of which is in its amorphous form and at least one other polymer additive wherein the additive has a melting point from about 35° C. to about 300° C.

It is still another aspect of the present invention to provide a solid phosphite composite containing at least one phosphite, at least some of which present in the amorphous form and at least one polymer additive therein such as a phenolic antioxidant, a hindered amine, or other additives such as a lactone stabilizer, an hydroxylamine, a benzoate, a 2-hydroxyphenyl benzotriazole, a 2-hydroxyphenyl benzophenone, an o-hydroxyphenyl-s-triazine, a phenylene-bis-benzoxazine-4-one, oxalic acid diamides, or a metal deactivator, an acid scavenger, and the like.

A phosphite composite of the present invention can be used as an additive package in various polymers such as polyolefin e.g. polyethylene or polypropylene, polycarbonate, polyester such as polyethyleneterephthalate, polyether, polyamide, polyimides, polystyrene, impact polystyrene, polyphenylene ether, acrylonitrile-butadiene-styrene graft polymer, polyurethane, polysulfone, polyacrylate, polyacetals, halide-containing polymer such as polyvinyl chloride, and the like.

DETAILED DESCRIPTION OF THE INVENTION

The melt blends of two or more phosphites optionally containing polymer additives such as a hindered phenolic antioxidant, light stabilizers such as a UV absorber or a hindered amine, or other additives such as a peroxide scavenger, a metal deactivator, a basic co-stabilizer, a nucleating agent, an optical brightener, an acid scavenger, and the like, are in the form of a solid composite wherein the different phosphites are randomly or uniformly distributed. Alternatively, a composite can contain one or more phosphites in a melt blend with one or more randomly or uniformly distributed polymer additives such as a hindered phenol, light stabilizers such as a UV absorber or a hindered amine, or other polymer additives described more fully herein below. A preferred phosphite is bis(arylalkylphenyl) pentaerythritol diphosphite. The phosphites serve as suitable antioxidants in various polymers such as polyolefins and have a low volatility, a high decomposition temperature and also retard yellowing of the polymer. The bis(arylalkylphenyl)pentaerythritol diphosphites are generally set forth in formula I as follows:

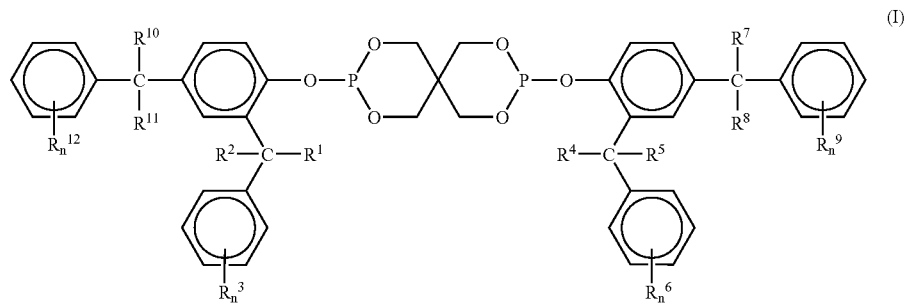

wherein $R^1$, $R^2$, $R^4$, $R^5$, $R^7$, $R^8$, $R^9$, $R^{10}$, $R^{11}$ are selectively independently from hydrogen, and alkyl of the generic formula $C_mH_{2m+1}$ and alkoxy radicals of general formula $C_mH_{2m+1}O$; wherein m ranges from 1 to 4; $R_n^3$, $R_n^6$, $R_n^9$, $R_n^{12}$, are selected independently from hydrogen, halogens, alkyl radicals of general formula $C_mH_{2m+1}$, and alkoxy radicals of general formula $C_mH_{2m+1}O$; wherein m ranges from 1 to 4; and further wherein n ranges from 0 to 3, and the substituent is located in a position ortho, meta, or para to the bridging methylene radicals. The halogens are preferably chlorine and bromine and impart a degree of fire retardancy to the polymer.

In particular, a preferred embodiment of the invention is a spiro diphosphite of formula II, bis(2,4-dicumylphenyl) pentaerythritol diphosphite:

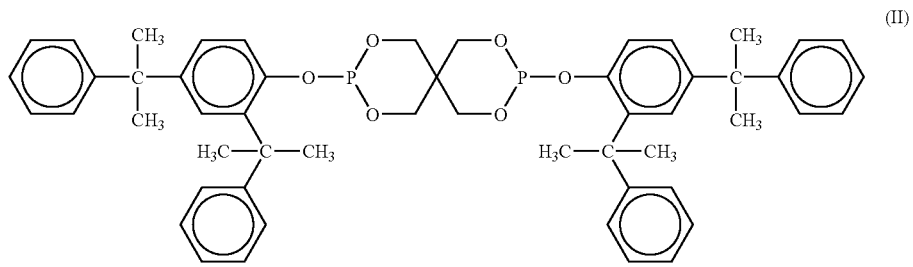

(II)

although depending on synthetic methods and conditions employed, a minor amount of the cage conformation can be present. Of course, it is possible to include a larger amounts of cage conformation in the final product, with the preparation of 10–15% cage conformation possible. The preparation and formation of the above noted bis(arylalkylphenyl) pentaerythritol diphosphites is set forth in U.S. Pat. No. 5,438,086; granted Aug. 1, 1995 to Stevenson and Kodali.

The above bis(arylalkylphenyl)pentaerythritol diphosphite such as preferably bis(2,4-dicumylphenyl)pentaerythritol diphosphite can be utilized with one or more other phosphites, either liquid or solid, to form the solid composite blend of the present invention. A non-limiting exemplary listing of other phosphites as well as phosphonites include at least the following with associated trademarks associated with the products of the applicant and others.

tris(2,4-di-tert-butylphenyl) phosphite
(Doverphos ® S-480)

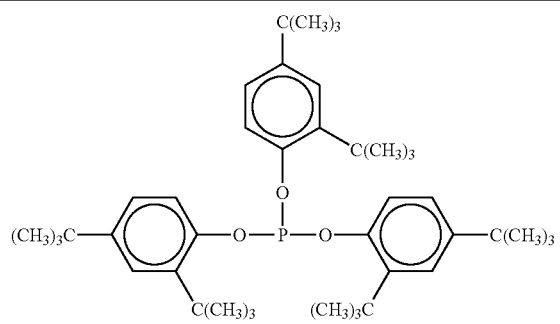

distearyl pentaerythritol diphosphite
(Doverphos ® S-680)

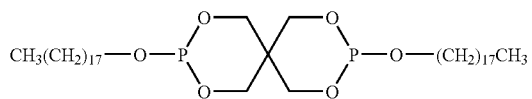

tris(nonylphenyl) phosphite
(Doverphos ® 4)

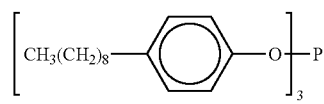

phenyl diisodecyl phosphite
(Doverphos ® 7)

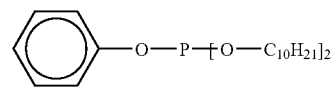

diphenyl isodecyl phosphite
(Doverphos ® 8)

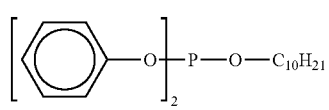

triphenyl phosphite
(Doverphos ® 10)

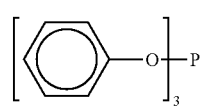

trilauryl phosphite
(Doverphos ® 53)

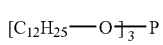

$C_{12-15}$ alkyl bis-phenol A (BPA) phosphite
(Doverphos ® 613)

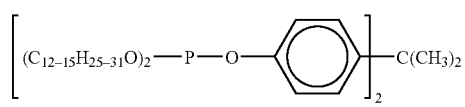

-continued

C₁₀ alkyl BPA phosphite
(Doverphos ® 675)

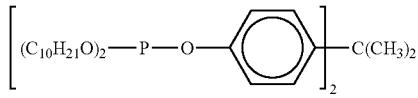

2-butyl-2-ethyl-1,3-propanediol 2,4,6-tri-tert-butylphenyl phosphite
(Ultranox ® 641)

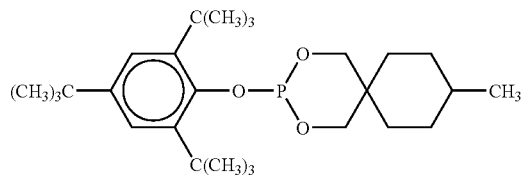

bis(2,6-di-tert-butyl-4-methylphenyl)pentaerythritol diphosphite
(PEP 36)

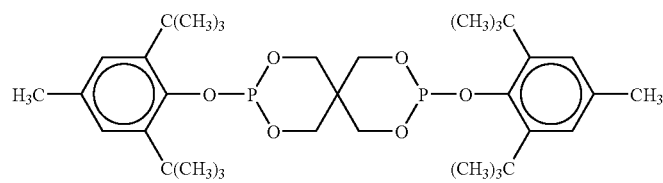

bis(2,4-di-tert-butyl)pentaerythritol diphosphite
(Doverphos ® 9432)

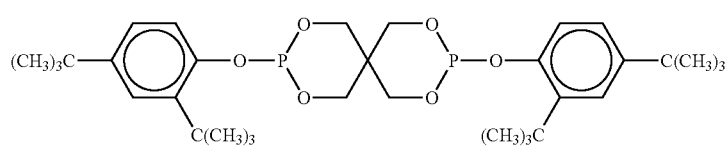

bis(2,4-di-tert-butyl-6-methylphenyl) ethyl phosphite
(Irgafos ® 38)

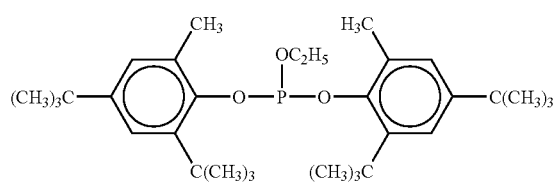

2,2',2''-nitrilotriethanol tris[3,3',5,5'-tetra-tert-butyl-1,1'-biphenyl-2,2'-diyl] phosphite
(Irgafos ® 12)

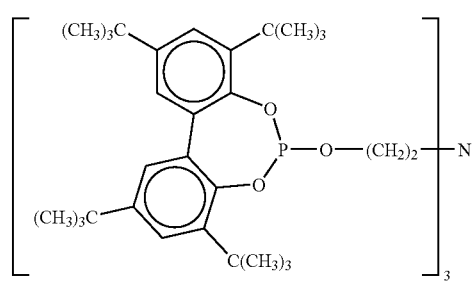

tetrakis-(2,4-di-tert-butylphenyl)-4,4'-diphenylene diphosphonite
(P-EPQ)

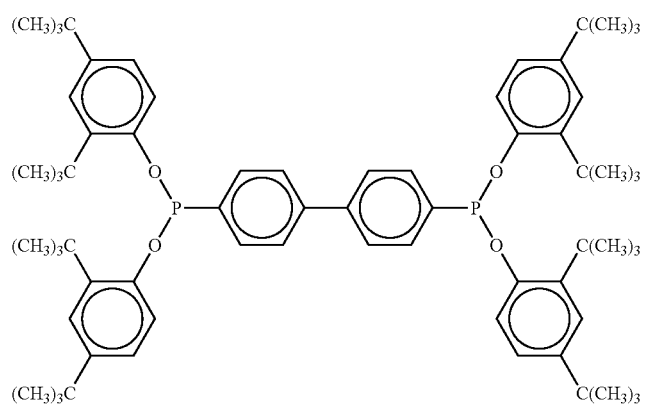

-continued

| | |
|---|---|
| 2,2'-ethylidene bis(4,6-di-tert-butylphenyl) fluorophosphonite (Ethanox ® 398) | 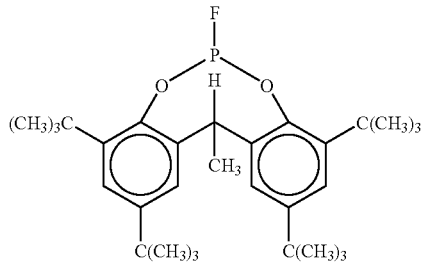 |

Generally, the amount of any amorphous blend phosphite such as the preferred bis(arylalkylphenyl)pentaerythritol diphosphite can vary from about 10 to about 90 parts and desirably from about 40 to about 90 parts by weight based on 100 total parts by weight of all of the phosphites in the composite. Should a liquid phosphite be utilized such as tris(nonylphenyl) phosphite (TNPP), the amount of bis(arylalkylphenyl)pentaerythritol diphosphite is such that the liquid phosphite during melt blending is absorbed therein with the final composite being a solid. In this situation, the amount of the bis(arylalkylphenyl)pentaerythritol diphosphite is generally from about 30 to 95 parts by weight, preferably from about 60 to 95 parts by weight based on the total weight of all the phosphites in the composite.

The two or more phosphites can be heated and/or mixed in any manner and/or order to a temperature above the melting point of each component, and blended. That is, the various phosphite components can be initially mixed, and subsequently heated, or initially heated to a melting temperature and subsequently mixed, or generally simultaneously mixed and heated to a melting temperature. Any conventional or known mixing and heating apparatus can be utilized to achieve a melt step where upon melting, the components are blended for a sufficient amount of time to achieve a random or uniform mixture. Once a uniform composite has been obtained, it is cooled (preferably rapidly) to below the melting point of the composite. This rapid cooling may be impinging upon a belt which is at room temperature or may be preceded by some pre-cooling in a jacketed vessel in which the amount of crystalline and amorphous material can be controlled by the use of external cooling means, the amorphous form acting in many cases, as a solvent for the crystalline form which is typically formed at the wall interface with the cooling means. Further control may be effected by temperature control of the belt which may initially be as high as a few degrees to 50° C. above room temperature (20–25° C.) and which progresses toward lower temperatures, e.g., 10–25° C. above room temperature, to even below room temperature, if desired. Preferably, the pouring, preferably dropping, the molten material onto a cool surface occurs at a temperature below 30° C., more preferably near 20–25° C. Preferably, the cool surface is a metal surface. It is recognized that the molten material can also be sprayed, preferably via nozzles, with a cooled gas onto a cool surface to form amorphous essentially spherical granules. The temperature of the cooled gas is preferably below 30° C. The amorphous solid thus obtained, can be further ground or granulated into any desired particle size by conventional means.

This composite, and the bis(arylalkylphenyl)pentaerythritol diphosphite component of the composite, generally shows unusual melt behavior, in that, when a sample of the material is heated, at some intermediate temperature above room temperature the material gives a clear melt, which then crystallizes to an opaque solid. On further heating, this solid gives a clear melt at a high temperature. For example, the single component bis(2,4-dicumylphenyl)pentaerythritol diphosphite (Formula II), when cooled rapidly from the melt, shows, by Differential Scanning Calorimetry (DSC), an initial small melt endotherm at 56.5° C. (illustrative of the amorphous form), two exothermic transitions at 111° C. and 152° C., and a final melt endotherm at 230° C. (illustrative of the crystalline form). The composite can be formed into any number of shapes such as particles, granules, prills, beads, flakes, ground powder, and the like as desired as by any conventional method. Should one of the components be a liquid, the remaining one or more of the phosphite components is heated above the melting point of the highest melting component and mixed to achieve a random or uniform distribution. Upon rapid cooling, the liquid component will be absorbed into the one or more solid components with a net result that a uniform, generally glassy or amorphous solid composite is formed. As noted above, mixing temperatures of generally from about 145° C. to about 300° C. are utilized inasmuch as the melting point of the preferred crystalline bis(arylalkylphenyl)pentaerythritol diphosphite is approximately 200° C. to 240° C.

In addition to or in lieu of the second or more phosphite compounds, numerous other polymer additives can be utilized so long as the melting temperature of the first phosphite compound or component is not detrimental to the additive.

One such additive are the various hindered phenol antioxidants. Such antioxidants can be utilized with any of the phosphite components whether or not the same is the preferred bis(arylalkylphenyl)pentaerythritol diphosphite. Examples of suitable hindered phenols include the following:

1.1 Alkylated mono-phenols, for example: 2,6-di-tert-butyl-4-methyl phenol, 2-tert-butyl-4,6-dimethyl phenol, 2,6-di-tert-butyl-4-ethyl phenol, 2,6-di-tert-butyl-4-n-butyl phenol, 2,6-di-tert-butyl-4-isobutyl phenol, 2,6-dicyclopentyl-4-methyl phenol, 2-(α-methylcyclohexyl)-4,6-dicyclopentyl-4-methyl phenol, 2,6-dioctadecyl-4-methyl phenol, 2,4,6-tricyclohexyl phenol, 2,6-di-tert-butyl-4-methoxymethyl phenol 1.2 Alkylated hydroquinones, for example: 2,6-di-tert-butyl-4-methoxy phenol, 2,5-di-tert-butylhydroquinone, 2,5-di-tert-amylhydroquinone, 2,6-diphenyl-4-octadecyloxyphenol.

1.3 Hydroxylated thiodophenol ethers, for example: 2,2'-thio-bis-(6-tert-butyl-4-methyl phenol), 2,2'-thio-bis-(4- octyl phenol), 4,4'-thio-bis(6-tert-butyl-3-methyl phenol), 4,4'-thiobis-(6-tert-butyl-2-methyl phenol).

1.4 Alkylidene bis-phenols, for example: 2,2'-methylene-bis(6-tert-butyl-4-methyl phenol), 2,2'-bis-(6-tert-butyl-4-ethyl phenol), 2,2'-methylene-bis-[4-methyl-6-(α-methylcyclohexyl) phenol], 2,2'-methylene-bis-(4-methyl-6-cyclohexyl phenol), 2,2'-methylene-bis-(6-nonyl-4-methyl phenol), 2,2'-methylene-bis-(6-nonyl-4-methyl phenol), 2,2'-methylene-bis-[6-(α-methylbenzyl)4-nonyl phenol], 2,2'-methylene-bis-[6-(α,α-dimethylbenzyl)4-nonyl phenol], 2,2'-methylene-bis-(4,6-di-tert-butyl phenol), 2,2'-ethylidene-bis-(6-tert-butyl-4-isobutyl phenol), 4,4'-methylene-bis-(2,6-di-tert-butyl phenol), 4,4'-methylene-bis-(6-tert-butyl-2-methyl phenol), 1,1-bis-(5-tert-butyl-4-hydroxy-2-methylphenol)-butane, 2,6-di-(3-tert-butyl-5-methyl-2-hydroxybenzyl)-4-methyl phenol, 1,1,3-tris-(5-tert-butyl-4-hydroxy-2-methyl phenyl)butane, 2,2-bis-(5-tert-butyl-4-hydroxy-2-methylphenyl)-3-dodecyl-mercaptobutane, ethyleneglycol-bis-(3,3-bis-(3'-tert-butyl-4'-hydroxyphenol) butyrate)-di-(3-tert-butyl-4-hydroxy-5-methylphenyl) dicyclopentadiene, di[2-(3'-tert-butyl-2'-hydroxy-5'-methyl-benzyl)-6-tert-butyl-4-methylphenyl] terephthalate, and other phenolics such as monoacrylate esters of bisphenols such as ethylidene bis-2,4-di-tert-butyl phenol monoacrylate ester.

1.5 Benzyl compounds, for example: 1,3,5-tris-(3,5-di-tert-butyl-4-hydroxybenzyl)-2,4,6-trimethyl benzene, bis-(3,5-di-tert-butyl-4-hydroxybenzyl)sulfide, isooctyl 3,5-di-tert-butyl-4-hydroxybenzyl-marcapto acetate, bis-(4-tert-butyl-3-hydroxy-2,6-dimethylbenzyl)dithiol terephthalate, 1,3,5-tris(3,5-di-tert-butyl-4-hydroxybenzyl(isocyanurate, 1,3,5-tris-(4-tert-butyl-3-hydroxy-2-6-dimethylbenzyl) isocyanurate, dioctadecyl 3,5-di-tert-butyl-4-hydroxybenzel phosphonate, 1,3,5-tris-(3,5-dicyclohexyl-4-hydroxybenzyl) isocyanurate.

1.6 Esters of beta-(5-tert-butyl-4-hydroxy-3-methylphenyl)propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.7 Esters of beta-(3,5-di-tert-butyl-4-hydroxyphenyl) propionic acid with monohydric or polyhydric alcohols, for example, methanol, diethylene glycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide.

1.8 Amides of beta-(3,5-di-tert-butyl-4-hydroxyphenyl) propionic acid for example, N,N'-di-(3,5-di-tert-butyl-4-hydroxyphenylpropionyl)hexamethylene diamine, N,N'-di-(3,5-di-tert-butyl-4-hydroxyphenylpropionyl) trimethylene diamine, N,N'-di-(3,5-di-tert-butyl-4-hydroxyphenylpropionyl) hydrazine.

Preferred hindered phenolic antioxidants include pentaerythritol tetrakis 3-(3,5-di-tert-butyl-4-hydroxyphenyl) propionate (Irganox® 1010), 2,6-di-tert-butyl-4-methylphenol (BHT), 2,6-di-tert-butyl-4-ethylphenol, octadecyl 3-(3,5-di-tert-butyl-4-hydroxyphenyl)propionate (Dovernox® 76), tris-(3,5-di-tert-butyl-4-hydroxybenzyl)-1,3,5-triazine-2,4,6-(1H, 3H, 5H)trione (Dovernox® 3114), 1,3,5-tris(4-tert-butyl-3-hydroxy-2,6-dimethylbenzyl)-isocyanurate (Cyanox® 1790) or α-tocopherol (Vitamin E), or combinations thereof. Most preferred antioxidants include BHT, pentaerythritol tetrakis 3-(3,5-di-tert-butyl-4-hydroxyphenyl) propionate, octadecyl 3-(3,5-di-tert-butyl-4-hydroxyphenyl) propionate, tris-(3,5-di-tert-butyl-4-hydroxybenzyl)-1,3,5-triazine-2,4,6(1H, 3H, 5H)-trione, and Vitamin E.

The amount by weight of the one or more hindered phenolic compounds to the one or more phosphites whether or not it includes the preferred bis(arylalkylphenyl)pentaerythritol diphosphite is generally from about 1 to about 99 parts by weight, and desirably from about 10 to 70 parts by weight based on 100 total parts by weight of all the hindered phenolic compounds and all the phosphite compounds.

Another type of polymer additive are the various light stabilizers, e.g. UV absorbers and hindered amines such as the following:

2.1 2-(2'-hydrosyphenyl)benzotriazoles, for example, the 5'-methyl-, 3',5'-di-tert-butyl-, 5'-(1,1,3,3-tetramethyl-butyl)-, 5-chloro-3',5'-di-tert-butyl-, 5-chloro-3'-tert-butyl-5'-methyl-, 3'-sec-butyl-5'-tert-butyl, 4'-octyloxy-, 3',5'-di-tert-amyl-, and 3',5'-bis(α,α-dimethylbenzyl)-derivatives.

2.2 2-hydroxybenzophenones, for example, the 4-hydroxy-, 4-methoxy-, 4-octyloxy-, 4-decyloxy-, 4-dodecyloxy-, 4-benzyloxy-, 4,2',4'-trihydroxy- and 2'-hydroxy-4,4'-dimethoxy derivatives.

2.3 Esters of substituted and unsubstituted benzoic acids for example, phenyl salicylate, 4-tert-butylphenyl-salicylate, octylphenyl salicylate, bis(4-tert-butylbenzoly) resorcinol, benzoyl resorcinol, 1 2',4'-di-tert-butylphenyl-3,5-di-tert-butyl-4-hydroxybenzoate and hexadecyl-3,5-di-tert-butyl-4-hydroxybenzoate.

2.4 Acrylates, for example, α-cyano-β,β-diphenylacrylic acid-ethyl ester or isoctyl ester, α-carbomethoxy-cinnamic acid methyl ester, α-cyano-β-methyl-p-methoxy-cinnamic acid methyl ester or butyl ester, α-carbomethoxy-cyano-vinyl)2-methyl indoline.

2.5 Sterically hindered amines, for example bis-(2,2,6,6-tetramethyl-4-piperidyl)-sebacate, bis-(1,2,2,6,6-pentamethyl-4-piperidyl) sebacate, n-butyl-3,5di-tert-butyl-4-hydroxybenzyl malonic acid-bis(1,2,2,6,6-pentamethyl-4-piperidyl) ester, condensation product of 1-hydroxyethyl-1,1,6,6-tetramethyl-4-hydroxy-piperidine and succinic acid, condensation product of N,N'-(2,2,6,6-tetramethylpiperidyl) hexamethylenediamine and 4-tert-octylamino-2,6 dichloro-1,3,5-s-triazine, tris-(2,2,6,6-tetramethyl-4-piperidyl)nitrilotriacetate, 1,6-hexanediamine, N,N'-bis-(2,2,6,6-tetramethyl-4-piperidinyl)-polymer with 2,4,6-trichloro-1,3,5-triazine, reaction products with N-butyl-1-butanamine and N-butyl-2,2,6,6-tetramethyl-4-piperidinamine, tetrakis-(2,2,6,6-tetramethyl-4-piperidyl)-1,2,3,4-butane-tetracarbonic acid, 1,1'-(1, 2-ethanediyl)-bis-(3,3,5,5-tetramethylpiperazin-2-one), tris-1,3,5-[N-cyclohexyl-N-{6-(3,3,5,5-tetramethylpiperazin-2-one)}hexyl]-2-triazine. These amines typically called HALS (Hindered Amine Light Stabilizers) include butane tetracarboxylic acid 2,2,6, 6-tetramethyl piperidinol esters. Such amines include hydroxylamines derived from hindered amines, such as di(1-hydroxy-2,2,6,6-tetramethylpipiridinyl) sebacate: 1-hydroxy-2,2,6,6-tetramethyl-4-benzyloxypiperidine: 1-hydroxy-2,2,6,6-tetramethyl-4-(3',5'-di-tert-butyl-4-hydroxy hydrocinnamoyloxy)-piperidine: and N-(1-hydroxy-2,2,6,6-tetramethyl-piperidin-4-yl) epsilon caprolactam.

2.6 Hydroxyphenyl-s-triazines, for example 2,6-bis(2,4-dimethylphenyl)-4-(2-hydroxy-4-octyloxyphenyl)-s-triazine; 2,6-bis(2,4-dimethylphenyl)4-(2,4-dihydroxyphenyl)-s-triazine; 2,4-bis(2,4-dihydroxyphenyl)-6-(4-chlorophenyl)-s-triazine; 2,4-bis(2-hydroxy-4-(2-hydroxyethoxy)-phenyl)-6-(2,4-dimethylphenyl)-s-triazine, 2,4-bis(2-hydroxy-4-(2-acetoxyethoxy) phenyl)-6-(4-chlorophenyl)l-s-triazine; 2,4-bis(2,4-dihydroxyphenyl)-6-(2,4-dimethylphenyl)-s-triazine.

Preferred Hindered Amine Light Stabilizers include bis-(1-octyloxy-2,2,6,6-tetramethyl-4-piperidinyl)-sebacate (Tinuvin 123), the polymeric condensation product of 1-hydroxyethyl-2,2,6,6-tetramethyl-4-hydroxy piperidine and succinic acid (Tinuvin 622), bis-(2,2,6,6-tetramethyl-4-piperidinyl)-sebacate (Tinuvin 770), 1,3,5-triazine-2,4,6-triamin-N,N "-[1,2-ethanediylbis{([4,6-bis(butyl{1,2,2,6,6-pentamethyl4-piperidinyl}amino)-1,3,5-triazine-2-yl]-3,1-propanediyl)}-bis-N,N'-bis(1,2,2,6,6-pentamethyl-4-piperidinyl)}] (Chimassorb 119),Poly-[(6-[(1,1,3,3-tetramethylbutyl)-amino]-s-triazine-2,4-diyl]-{[(2,2,6,6-tetramethyl4-piperidinyl)-imino]-hexamethylene-[(2,2,6,6-tetramethyl-4-piperidinyl)-imino]] (Chimassorb 944), and combinations thereof.

The amount by weight of the one or more light stabilizing additives to the one or more phosphites whether or not it includes the preferred bis(arylalkylphenyl)pentaerythritol diphosphite is generally from about 1 to about 99 parts by weight, and desirably from about 10 to about 70 parts by weight based upon 100 total parts by weight of all the light stabilizer compounds and all the phosphite compounds.

If both light stabilizers as well as hindered phenols are utilized, the above amounts by weight are based upon 100 total parts by weight of all phosphites, all light stabilizers, and all hindered phenols.

Many other polymer additives can be incorporated into the melt blend which can contain one or more of the above noted phosphites and one or more of the above noted hindered phenol compounds. These additional polymer additives include metal deactivators, peroxide scavengers, acid scavengers such as calcium stearate, zinc stearate, calcium lactate, calcium stearol-2-lactate epoxidized soybean oil, and hydrotalcite (natural and synthetic), basic co-stabilizers, nucleating agents, reinforcing agents, plasticizers, lubricants, emulsifiers, pigments and dyes, optical brighteners, flame-proofing agents, antistatic agents, blowing agents, cross-linking agents, antiblocking agents, slip agents, processing aids, and thiosynergist. Specific examples of these polymer additives are disclosed in U.S. Pat. No. 5,438,086. Additionally, lactone stabilizers such as 5,7-bis (1,1-dimethylethyl)-3-phenyl-2-(3H )-benzofuranone; 5-nonyl-3-phenyl-2-(3H)-benzofu ranone; 5-(1,1,3,3-tetramethylbutyl)-3-phenyl-2-(3H)-benzofuranone; and 5,7-bis(1,1-dimethylethyl)-3-(3,4-dimethylphenyl(-2-(3H)-benzofuranone (HP-136 from Ciba-Geigy) can also be used in these blends.

The amount of these other polymer additives can be from about 2 parts to about 98 parts by weight and preferably from about 5 parts to about 70 parts by weight based on a total of 100 parts by weight of all the polymer additives, all of the one or more phosphites, all of the one or more light stabilizers, and all of the any one or more hindered phenols.

The melting point of the one or more polymer additives generally ranges from about 35° C. to about 300° C. and thus is melted along with the one or more phosphite compounds and melt blended by thoroughly mixing to produce a uniform or randomly distributed mixture. Alternatively, one or more of the polymer additives can be liquid but is utilized with a sufficient amount of the remaining polymer additives or one or more phosphite compounds such that upon melt mixing a solid phosphite composite is produced.

The preparation of composites of the present invention utilizing one or more phosphites with either one or more hindered phenols, or one or more light stabilizers, and/or one or more polymer additives is essentially the same as set forth above with regard to melt blending two or more phosphites. That is, the various components are heated to a melting temperature which melts the one or more phosphites, and the one or more hindered phenols and/or light stabilizers, and/or polymer additives, mixing and blending the same to achieve a random or uniform mixture, and cooling. The composite can then be shaped into any conventional size, such as the pellets, granules, etc.

The melt blend composites of the present invention can be utilized with numerous polymers such as polyolefins particularly polyethylene and polypropylene, polycarbonates, polyesters such as polyethylene terephthalate, polyamides (nylons), polyimines, polystyrene, polyphenylene ether, ABS-type graft copolymers, polyurethanes, polysulfone, polyacrylates, polyacetals, and halide-containing polymers such as polyvinyl chloride. Specific examples of these as well as other polymers which can be utilized are set forth in U.S. Pat. No. 5,438,086.

The melt composites of the present invention can contain some, most, and even all of the necessary compounding ingredients which are utilized in the preparation of various polymers for specific uses. The preparation of such melt blended composites containing the above noted components results in a blend which is very suitable or convenient to use. Another advantage is that a great majority of all of the various additives can be prepared as solid phosphite composite package so that only the phosphite-additive package need be added to a polymer and blended therewith. The use of such a package further results in the abatement or elimination of dusting problems. Another advantage is that weighing errors are reduced in as much as a large amount of a particular composite can be made and since the same is uniform. When the preferred phosphite is utilized, i.e. bis (arylalkylphenyl) pentaerythritol diphosphite, better protection is generally obtained against polymer degradation due to oxidation than is currently available with regard to commercial blends. Still another advantage is the synergistic performance obtained in the stabilization of polymers as opposed to the utilization of any single phosphite. Yet still another advantage is that in using the hydrolytically stable bis(arylalkylphenyl)pentaerythritol diphosphite as described in U.S. Pat. No. 5,438,086, in combination in the melt blend with another phosphite or other polymer additive which is sensitive to hydrolysis under exposure to atmospheric humidity, such as bis(2,4-di-tert-butylphenyl) pentaerythritol diphosphite and bis(2-tert-butyl-4-{α,α'-dimethylbenzyl} pentaerythritol diphosphite, the melt blend of the phosphites and/or the other polymer additive shows markedly enhanced hydrolytic stability on exposure to moisture in the air. Moreover, the various additives utilized in a melt blend composite can be tailor made to produce a compounded polymer having desired properties.

The invention will be better understood by reference to the following examples which serve to illustrate but not to limit the present invention.

EXAMPLE #1

Preparation of a 90:10 Blend of Amorphous Doverphos® S-9228 and TNPP

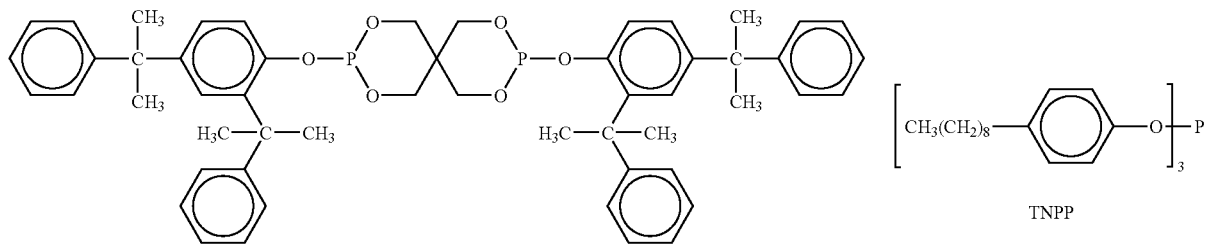

Doverphos® S-9228

TNPP

In a weighing dish add 9 grams of crystalline Doverphos® S-9228, 1.0 grams of TNPP, mix them well and add a 25 ml. test tube. The test tube is immersed in an oil bath, under an $N_2$ blanket, which was preheated to 235–240° C. The blend was completely melted within 15 minutes. The hot liquid was transferred into droplets, via a dropper, onto an aluminum foil at room temperature.

The liquid droplets became solid, glassy beads as it cooled to 20° C. The resultant beads were dry and free flowing and there is no tackiness due to the present of liquid TNPP. A sample of the glassy product showed an initial melt transition to a partially crystalline phase at 73–93° C., and final melting to a clear melt at 225–230° C., The DSC of this material showed an initial endothermic transition at 52° C. (amorphous phase), exothermic melt transitions at 90° C., 98° C. and 124° C., and a final endothermic transition at 220° C.

EXAMPLE #2

Preparation of an 80:20 Blend of Amorphous Doverphos® S-9228 and TNPP

The same procedure as Example #1 was followed, but with 8 grams of Doverphos® S-9228 and 2 grams of TNPP, and gave free flowing beads. A sample of the glassy product on heating showed an initial transition to a partially crystalline phase at 61–85° C., and a final melting to a clear melt at 224–226° C. The DSC showed exothermic transitions at 90° C. and 141° C. and an endothermic transition at 228° C.

EXAMPLE #3

Preparation of a 70:30 Blend of Amorphous Doverphos® S-9228 and TNPP

The same procedure as in Example #1 was followed, but with 7 grams of Doverphos® S-9228 and 3 grams of TNPP, and gave free-flowing beads. A sample of the glassy product showed an initial melt transition to a partially crystalline phase at 52–85° C. and a final melting to a clear melt at 220–222° C. the DSC showed an exothermic transition at 130° C. and an endothermic transition at 223° C.

EXAMPLE #4

Preparation of a 50:50 Blend of Amorphous Doverphos® S-9228 and tris-(2,4-di-tert-butylphenyl)phosphite (Doverphos® S-480)

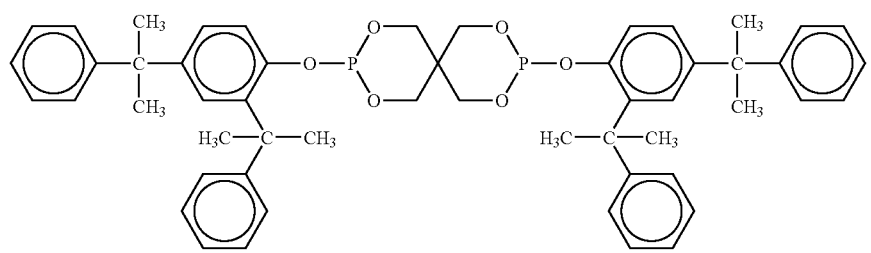

Doverphos® S-9228

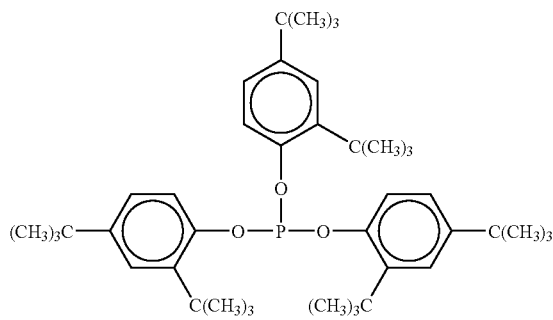

Doverphos® S-480

The same procedure as in Example #1 was followed, but with 5 grams of Doverphos® S-9228 and 5 grams of tris-(2,4-di-tert-butyl phenyl) phosphite, and gave free flowing beads. A sample of the glassy product showed an initial melt transition to a partially crystalline phase at 75° C., and a final melting to a clear melt at 210–214° C. The DSC showed an initial endothermic transition at 51° C., three exothermic transitions at 104, 108 and 158° C., and three endothermic transitions at 182° C., 202° C. and 211° C.

EXAMPLE #5

Preparation of a 50:25:25 Blend of Amorphous Doverphos® S-9228, TNPP and tris(2,4-di-tert-butylphenyl) phosphite (Doverphos® S-480)

The same procedure as in Example #1 was followed, but with 5 grams of Doverphos® S-9228, 2.5 grams of TNPP, and 2.5 grams of tris(2,4-di-tert-butylphenyl) phosphite (Doverphos® S-480), and gave free flowing dry beads. A sample of the glassy product showed an initial melt transition to a partially crystalline phase at 75° C. and a final melting to a clear melt at 210–213° C.

EXAMPLE #6

Preparation of a 60:20:20 Blend of Amorphous Doverphos® S-9228, TNPP and Ultranox® 626

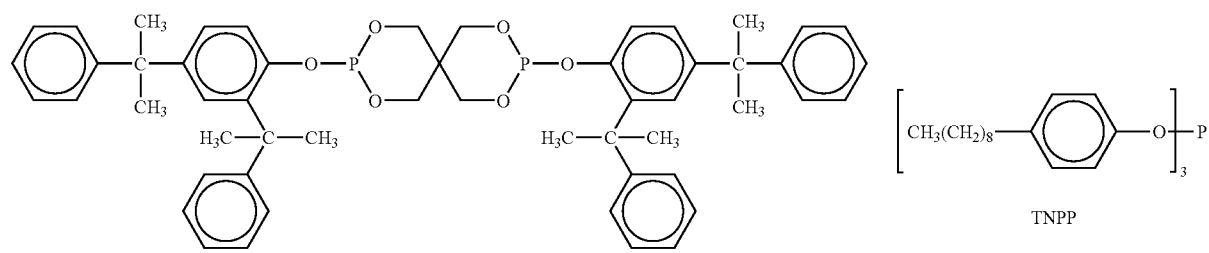

Doverphos® S-9228                    TNPP

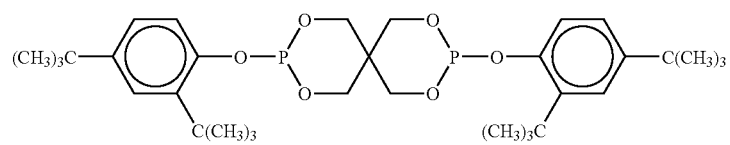

Ultranox® 626

The same procedure as in Example #1 was followed, but with 6 grams of Doverphos® S-9228, 2 grams of TNPP, and 2 grams of Ultranox® 626. The material was obtained as free flowing beads.

EXAMPLE #7

Preparation of a 66:22:12 Blend of Amorphous Doverphos® S-9228. BHT and Dovernox® 10

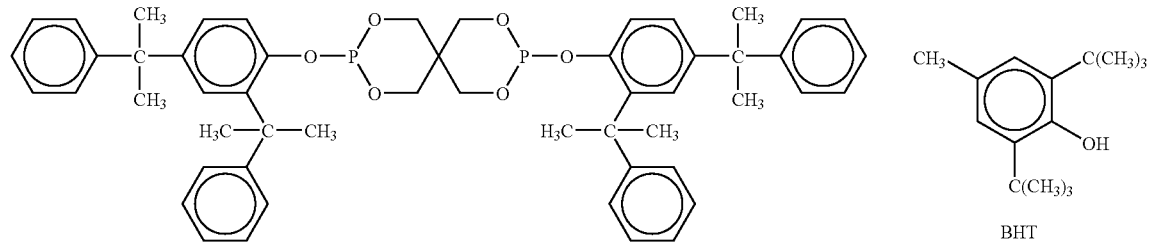

Doverphos® S-9228

Dovernox® 10

The same procedure as in Example #1 was followed, but with 6.6 grams of Doverphos® S-9228, 2.2 grams of BHT, and 1.2 grams of Dovernox® 10. The material was obtained as free flowing dry beads. A sample of the glassy material showed an initial melt transition to a partially crystalline phase at 57–80° C. and a final melting to a clear melt at 207–212° C.

EXAMPLE #8

Preparation of a 55:20:23:2 Blend of Amorphous Doverphos® S-9228, tris-(2,4-di-tert-butylphenyl) phosphite (Dovernox® S-480). TNPP and Vitamin E The same procedure as in Example #1 was followed, but with 5.5 grams of Doverphos® S-9228, 2.0 grams of tris-(2,4-di-tert-butylphenyl) phosphite (Dovernox® S-480), 2.3 grams of TNPP and 0.2 grams of vitamin E. The material was obtained as free flowing beads. The DSC of the material showed three exothermic transitions at 80° C., 132° C. and 165° C., and an endothermic transition at 219° C.

EXAMPLE #9

Preparation of a 50:50 Blend of Amorphous Doverphos® S-9228 and Ultranox® 641

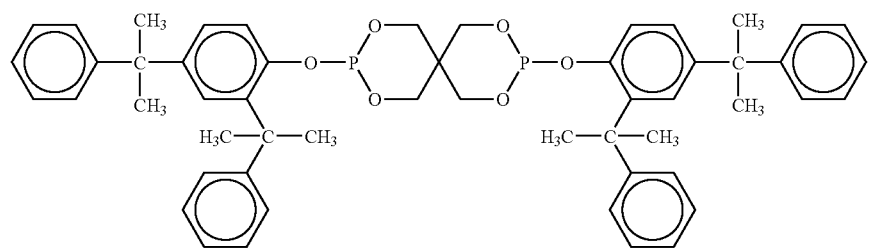

Doverphos® S-9228

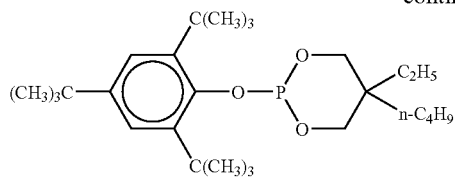

Ultranox® 641

The same procedure as in Example #1 was followed, but with 5 grams of Doverphos® S-9228 and 5 grams of Ultranox® 641 and gave dry, free flowing beads. A sample of the glassy material showed an initial melt transition to a partially crystalline phase at 62° C. and a final melting to a clear melt at 205–211° C.

EXAMPLE #10

Preparation of an 80:20 Blend of Amorphous Doverphos® S-9228 and bis-(2.2.6.6-tetramethyl-4-piperidinyl)-sebacate (Tinuvin® 770)

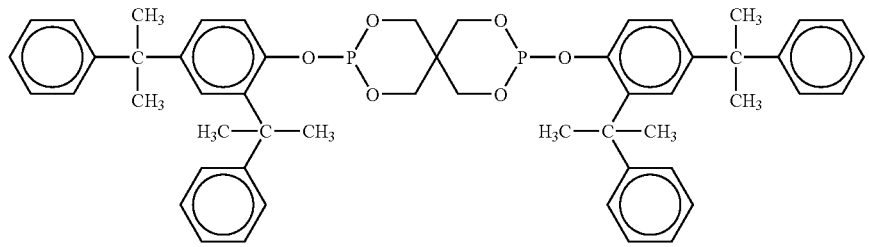

Doverphos® S-9228

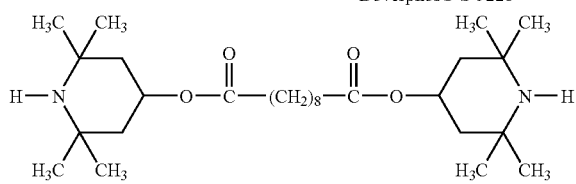

Tinuvin® 770

The same procedure as in Example #1 was followed but with 8 grams of Doverphos® S-9228 and 2 grams of Tinuvin® 770 and gave dry, free flowing beads. A sample of the opaque glassy material showed an initial melt transition to a partially crystalline phase at 82–110° C. and a final melting to a clear melt at 215–220° C. The DSC showed two exothermic transitions at 83° C. and 133° C., and an endothermic transition at 225° C.

EXAMPLE #11

Preparation of an 80:20 Blend of Amorphous Doverphos® S-9228 and poly[{6-(1,1,3.3-tetramethylbutyl)-amino}-s-triazine-2,4-diyl]-[{(2,2,6.6-tetramethyl-4-piperidyl)-imino}-hexamethylene-{(2.2,6,6-tetramethyl-4-piperidyl)-imino}] (Chimassorb® 944)

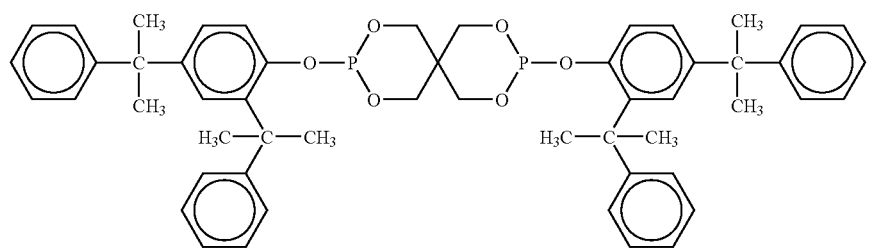

Doverphos® S-9228

-continued

[Chemical structure of Chimassorb® 944]

Chimassorb® 944

The same procedure as in Example #1 was followed, but with 8 grams of Doverphos® S-9228 and 2 grams of Chemosorb® 944 and gave dry, free flowing beads. A sample of the glassy material showed an initial melt transition to a partially crystalline phase at 82–110° C. and a final melting to a clear melt at 215–220° C. The DSC showed an initial endothermic transition at 62° C., two exothermic transitions at 111° C. and 179° C., and an endotherm at 229° C.

EXAMPLE #12

Preparation of an 80:20 Blend of Amorphous Doverphos® S-9228 and P-EPQ

The same procedure as in Example #1 was followed, but with 8 grams of Doverphos® S-9228 and 2 grams of P-EPQ, and gave free flowing dry beads. A sample of the glassy material showed a melting point of 219–220° C. The DSC showed an initial endothermic transition at 66° C., two exothermic transitions at 126° C. and 177° C., and endothermic transitions at 213° C. and 225° C.

EXAMPLE #13

Preparation of an 80:20 Blend of Amorphous Doverphos® S-9228 and Doverphos® S-680

The same procedure as in Example #1 was followed but with 8 grams of Doverphos® S-9228 and 2 grams of Doverphos® S-680, and gave dry, free flowing beads. A sample of the glassy material showed a melting point at 215–220° C.

EXAMPLE #14

Preparation of an 80:20 Blend of Amorphous Doverphos® S-9228 and Dovernox® 3114

The same procedure as in Example #1 was followed but with 8 grams of Doverphos® S-9228 and 2 grams of Dovernox® 3114 and gave dry, free flowing beads. A sample of the glassy material showed an initial melt transition to a partially crystalline phase at 85–120° C. and a final melting to a clear melt at 223–226° C. The DSC showed an initial endothermic transition at 62° C., two exothermic transitions at 129° C. and 175° C., and two endothermic transitions at 205° C. and 228° C.

EXAMPLE #15

Preparation of a 50:50 Blend of Amorphous Doverphos® S-9228 and Ultranox® 626

The same procedure as in Example #1 was followed but with 5 grams of Doverphos® S-9228 and 5 grams of Ultranox® 626 and gave dry, free flowing beads. A sample of the glassy material showed an initial melt transition to a partially crystalline phase at 75–113° C. and a final melting to a clear melt at 211–216° C.

EXAMPLE #16

Preparation of an 80:20 Blend of Amorphous Doverphos® S-9228 and Doverphos® S-680

The same procedure as in Example #1 was followed but with 8 grams of Doverphos® S-9228 and 2 grams of Doverphos® S-680 and gave dry, free flowing beads. A sample of the glassy material showed an initial melt transition to a partially crystalline phase at 140° C. and a final melting to a clear melt at 214–217° C. The DSC showed an initial exothermic transition at 140° C., and endothermic transitions at 214° C. and 217° C.

Polypropylene Evaluation

The above solid belt blended composites (with the Doverphos® S-9228 in its amorphous crystalline phase) were evaluated in polypropylene for heat stability. The results are shown in the following tables:

| Formulation: | Parts |
| --- | --- |
| Polypropylene PP 6501, Hercules | 100 |
| Calcium Stearate | 0.05 |
| Dovernox ® 10 | 0.05 |
| [Chemical structure: HO-C₆H₂(C(CH₃)₃)₂-C₂H₄-C(=O)-O-CH₂-C, bracketed ×4] | |
| Phosphite additive | 0.05 |

The above formulation was processed in a Brabender Extruder Model PL2000, at 280° C. with 60 RPM screw, and melt flow index (MFI) of the extruded resin was measured using a Tinius Olsen Melt index measuring instrument after 1, 3 and 5 passes through the extruder. The yellowness index (YI) of the extruded resin was measured after compression molding of the extruded resin into a 2 mil. thick plate using a Wabash Genesis model compression molding machine at 190° C.

The data in Table I gives performance data of blends of bis(2,4-dicumylphenyl)pentaerythritol diphosphite (Doverphos® S-9228) and tris(nonylphenyl) phosphite (TNPP).

TABLE I

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 1 | None | 8.9 | 12.1 | 18.0 | 5.2 | 6.5 | 8.5 |
| 2 | Doverphos ® S-9228 (crystalline) | 3.9 | 4.5 | 6.5 | 3.9 | 5.2 | 6.3 |
| 3 | Doverphos ® S-9228/ TNPP 90/10 (amorphous blend) | 3.5 | 4.5 | 5.5 | 3.7 | 4.7 | 6.2 |
| 4 | Doverphos ® S-9228/ TNPP 80/20 (amorphous blend) | 5.0 | 5.5 | 6.4 | 4.4 | 6.1 | 7.7 |
| 5 | Doverphos ® S-9228/ TNPP 70/30 (amorphous blend) | 5.8 | 7.0 | 7.6 | 4.1 | 4.8 | 5.8 |
| 6 | TNPP (liquid) | 5.7 | 6.5 | 6.7 | 5.1 | 6.4 | 8.2 |

It is clear from the data in the table that a blend of phosphites, comprising an amorphous Doverphos® S-9228 and a liquid phosphite (TNPP), particularly at a ratios of 90/10 and 70/30 outperformed the use of either phosphite individually. Even at a ratio of 80/20, the performance was similar to that of the benchmark of crystalline S-9228 alone. Without being held to any one theory of operation, it is believed that the value of having all or at least a portion of the Doverphos® S-9228 in an amorphous form resides in the superior distribution of the phosphite in the polypropylene polymer at lower processing temperatures. Therefore, it is surprising that amorphous blends performed equivalently, and in some instances, better than the benchmark crystalline S-9228 additive in the table.

The data in Table II gives performance data on an amorphous melt blend of Doverphos® S-9228 and Doverphos® S-480 in comparison to either additive added individually.

TABLE II

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 1 | None | 8.9 | 12.1 | 18 | 5.2 | 6.5 | 8.5 |
| 2 | Doverphos ® S-9228 (crystalline) | 3.9 | 4.5 | 6.5 | 3.9 | 5.2 | 6.3 |
| 3 | Doverphos ® S-9228/ S-480 50/50 (amorphous blend) | 4.9 | 7.6 | 9.7 | 3.7 | 4.4 | 5.1 |
| 4 | S-480 (crystalline) | 6.1 | 9.1 | 13.5 | 4.0 | 5.3 | 6.3 |

Once again, what is shown is the 50/50 amorphous blend outperformed either crystalline phosphite when added individually, an unexpected result.

The data in Table III gives performance data on an amorphous blend of Doverphos® S-9228 and Ultranox® 626 in contrast to either crystalline product added individually.

TABLE III

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 1 | None | 8.9 | 12.1 | 18.0 | 5.2 | 6.5 | 8.5 |
| 2 | Doverphos ® S-9228 (crystalline) | 3.9 | 4.5 | 6.5 | 3.9 | 5.2 | 6.3 |
| 3 | Doverphos ® S-9228/626 50/50 (amorphous blend) | 4.4 | 6.1 | 9.2 | 4.0 | 4.8 | 5.4 |
| 4 | Ultranox ® 626 (crystalline) | 4.0 | 5.4 | 6.1 | 3.7 | 5.4 | 6.1 |

The ability to resist yellowing through multiple extrusion passes is once again clearly demonstrated by the superior performance of the amorphous phosphite blend. It is noted that the amorphous blend clearly showed superior efficacy in the polypropylene polymer when compared to either known crystalline state-of-the art additive when added individually, an unexpected result.

The data in Table IV gives performance data on an amorphous blend of Doverphos® S-9228 and Ultranox® 641 in comparison to either crystalline product added individually.

TABLE IV

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 1 | None | 8.9 | 12.1 | 18.0 | 5.2 | 6.5 | 8.5 |
| 2 | Doverphos ® S-9228 (crystalline) | 3.9 | 4.5 | 6.5 | 3.9 | 5.2 | 6.3 |
| 3 | Doverphos ® S-9228/ 641 50/50 (amorphous blend) | 4.4 | 4.9 | 5.8 | 3.5 | 4.6 | 5.3 |
| 4 | Ultranox ® 641 (crystalline) | 4.1 | 6.0 | 7.0 | 4.2 | 5.5 | 7.9 |

Once gain, the value of the amorphous blend is easily seen and unexpected.

The data in Table V gives performance data on ternary and quaternary amorphous blends of Doverphos® S-9228 and additional components.

TABLE V

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 1 | None | 8.9 | 12.1 | 18.0 | 5.2 | 6.5 | 8.5 |
| 2 | S-9228/TNPP/S-480/ Vitamin E 55/23/ 20/2 (amorphous blend) | 6.0 | 6.4 | 6.9 | 3.8 | 5.1 | 6.4 |
| 3 | S-9228/BHT/ Dovernox ® 10 66/22/12 (amorphous blend) | 4.2 | 5.7 | 7.0 | 4.0 | 5.0 | 5.9 |
| 4 | S-9228/TNPP/ Ultranox ® 626 60/20/20 (amorphous blend) | 4.2 | 5.7 | 7.0 | 4.0 | 5.3 | 6.7 |

TABLE V-continued

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 5 | S-9228/TNPP/S-480 50/25/25 (amorphous blend) | 6.1 | 5.9 | 7.4 | 3.4 | 4.6 | 5.6 |

The value in synthesizing amorphous blends of which include more than binary blends, e.g., Vitamin E, Dovernox® 10, Ultranox® 626 and Doverphos® S-480 in addition to Doverphos® S-9228 and liquid TNPP is once again clearly shown in the above table.

The melt blend composites of Example #10, 11, 12, 13, 14 and 16 were evaluated in Polypropylene by the evaluation method above, but using a different batch of PP 6501 Polypropylene, with a higher melt flow index of the starting formulation without phosphite composite. The data in Table VI gives performance data on amorphous blends of Doverphos® S-9228 and other stabilizers as well as a comparison to amorphous S-9228 used individually.

TABLE VI

| | | MFI | | | YI | | |
|---|---|---|---|---|---|---|---|
| # | Stabilizer Blend | 1st Pass | 3rd Pass | 5th Pass | 1st Pass | 3rd Pass | 5th Pass |
| 1 | None | 11.2 | 24.6 | 43.1 | 4.5 | 7.1 | 10.3 |
| 2 | S-9228/S-682 80/20 (amorphous blend) | 6.2 | 14.1 | 18.3 | 4.2 | 5.1 | 6.5 |
| 3 | S-9228/Chimassorb ® 944 80/20 (amorphous blend) | 7.5 | 13.4 | 20.5 | 3.7 | 4.5 | 5.0 |
| 4 | S-9228/Dovernox ® 3114 80/20 (amorphous blend) | 7.1 | 9.4 | 15.3 | 4.0 | 4.9 | 5.6 |
| 5 | S-9228/P-EPQ 80/20 (amorphous blend) | 6.5 | 9.7 | 17.6 | 4.0 | 4.9 | 5.6 |
| 6 | S-9228/S-680 80/20 (amorphous blend) | 7.4 | 12.0 | 18.3 | 3.6 | 4.3 | 5.1 |
| 7 | S-9228/Tinuvin ® 770 80/20 (amorphous blend) | 7.4 | 13.7 | 22.6 | 3.5 | 4.3 | 4.8 |
| 8 | S-9228 (amorphous) | 6.5 | 10.9 | 17.5 | 3.9 | 4.3 | 5.0 |

As is seen in the table, the incorporation of various second phosphites and/or phosphonites into an amorphous Doverphos® S-9228 blend demonstrated similar, and sometimes, superior performance characteristics.

The hydrolytic stability of one melt blend of Doverphos® S-9228 and a second phosphite was tested against the individual powders, a melt of Doverphos® S-9228, and a powder blend of the phosphites. The hydrolytic stability data is shown in Table VII.

TABLE VII

Hydrolytic Stability
After 24 Hours at 55° C. and 85% Relative Humidity

| Phosphite | % weight gain | Acid Value (initial) | Acid Value (24 Hours) |
|---|---|---|---|
| Ultranox ® 626 (crystalline powder) | 16 | 1.0 | 95 |
| Doverphos ® S-9228/Ultranox ® 626 50/50 (crystalline powder blend) | 16 | 0.5 | 100 |

TABLE VII-continued

Hydrolytic Stability
After 24 Hours at 55° C. and 85% Relative Humidity

| Phosphite | % weight gain | Acid Value (initial) | Acid Value (24 Hours) |
|---|---|---|---|
| Doverphos ® S-9228/Ultranox ® 626 (amorphous melt blend) | 14 | 0.1 | 75 |
| Doverphos ® S-9228 (amorphous melt) | 11 | 0.1 | 31 |
| Doverphos ® S-9228 (crystalline powder) | 1.0 | 0.1 | 1.0 |

The date in Table VIII offers some technical insight into at least part of the reason for the efficacy of amorphous melt blends in contrast to the incorporation of compacted crystalline material. Both 1:1 and 2:1 blends of amorphous Doverphos® S-9228 and Dovernox® 10 (DN) were synthesized and compared with compacted crystalline blends of the same. The samples were dispersed in polypropylene (PP6301) at 180° C. using the olefin screw and compression molded plaques to 0.025" (0.0635 cm) and observed, under magnification, the presence of any unmelted additive as evidenced by the number of specks observed.

TABLE VIII

| | Blend (ppm) | | | |
|---|---|---|---|---|
| | A | B | C | D |
| S-9228/DN 10 (1:1 crystalline mixture) | 1000 | | | |
| S-9228/DN 10 (2:1 crystalline mixture) | | 1000 | | |
| S-9228/DN 10 (1:1 amorphous blend) | | | 1000 | |
| S-9228/DN 10 (2:1 amorphous blend) | | | | 1000 |
| # of specks | 9 (small) | 10 (small) | 4 (smaller) | 8 (smaller) |

As shown in the table, the fewest specks were observed with the amorphous blends, and in addition, the specks observed were smaller in size than those observed with the crystalline mixtures, leading support for the conclusion that the amorphous melt blends with their lower melting points, are incorporated into the lower processing temperature polymers better than standard compacted crystalline mixtures.

Therefore, unlike the Prior Art which at best taught the use of an amorphous form of a hindered phenolic in amorphous form, the applicant has invented a more direct route by switching the emphasis toward the amorphous phosphite, particularly bis(2,4-dicumylphenyl)pentaerythritol diphosphite, a path not seen by the Prior Art. The lower melting point is believed to result in better distribution within polymers thereby more effectively blocking various degradation paths.

While in accordance with the Patent Statutes the best mode and preferred embodiment have been set forth, the scope of the invention is not limited thereto but rather by the scope of the attached claims.

What is claimed is:

1. A process for forming amorphous bis(2,4-dicumylphenyl)pentaerythritol diphosphite of formula (II)

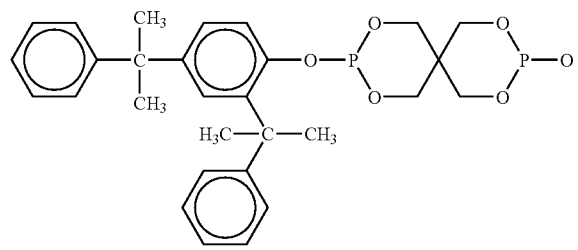

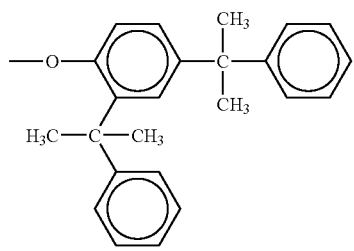

comprising the steps of:
(a) heating a crystalline form of said bis(2,4-dicumylphenyl)pentaerythritol diphosphite to a temperature to effect melting of said crystalline form of said diphosphite; and
(b) cooling said melted diphosphite to form an amorphous solid bis(2,4-dicumylphenyl)pentaerythritol diphosphite having an initial melting point of between approximately 50° C. and 65° C.

2. The process of claim 1 wherein said step of heating is from 200° C. to 300° C. inclusive.

3. The process of claim 2 wherein said step of cooling comprises at least the step of impinging said melt onto a surface at a temperature of about 50° C. or below.

4. The product of the process of claim 3.

5. The process of claim 1 which further comprises the step of adding at least one second additive to said diphosphite.

6. The process of claim 5 wherein said at least one second additive is selected from the group consisting of phosphites and phosphonites.

7. The process of claim 6 wherein which further comprises the step of adding at least one third additive to said diphosphite.

8. The process of claim 7 wherein said at least one third additive is selected from the group consisting of hindered phenolic antioxidants and hindered amine light stabilizers.

9. The process of claim 8 which further comprises the step of adding at least one fourth additive selected from the group consisting of metal deactivators, peroxide scavengers, acid scavengers, basic co-stabilizers, nucleating agents, reinforcing gents, plasticizers, lubricants, emulsifiers, pigments, dyes, optical brighteners, flame-proofing agents, antistatic agents, blowing agents, crosslinking agents, antiblocking agents, slip agents, processing aids and thiosynergists.

10. A process for forming amorphous bis(2,4-dicumylphenyl)pentaerythritol diphosphite of formula (II)

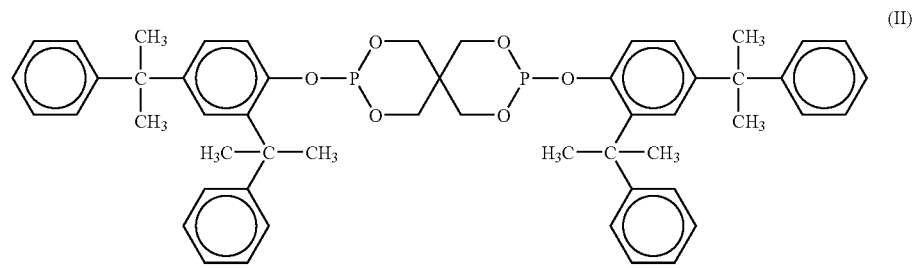

melt composite comprising the steps of:
  (a) heating a crystalline form of said bis(2,4-dicumylphenyl)pentaerythritol diphosphite to a temperature to effect melting of said diphosphite;
  (b) adding at least one second additive to said diphosphite and mixing therein to form a melt composite; and
  (c) cooling said melt composite to below to form a solid melt composite, at least a portion of which is amorphous bis(2,4-dicumylphenyl)pentaerythritol diphosphite having an initial melting point between approximately 50° C. and 65° C.

11. The process of claim 10 wherein said step of heating is from 200° C. to 300° C. inclusive.

12. The process of claim 11 wherein said step of cooling comprises at least the step of impinging said melt composite onto a surface at a temperature of about 50° C. or below.

13. The process of claim 10 wherein said at least one second additive is selected from the group consisting of phosphites and phosphonites.

14. The process of claim 13 wherein said step of adding further comprises adding at least one third additive.

15. The process of claim 14 wherein said at least one third additive is selected from the group consisting of hindered phenolic antioxidants and hindered amine light stabilizers.

16. The process of claim 15 which further comprises the step of adding at least one fourth additive selected from the group consisting of metal deactivators, peroxide scavengers, acid scavengers, basic co-stabilizers, nucleating agents, reinforcing gents, plasticizers, lubricants, emulsifiers, pigments, dyes, optical brighteners, flame-proofing agents, antistatic agents, blowing agents, crosslinking agents, antiblocking agents, slip agents, processing aids and thiosynergists.

17. A process for improving the melt stability of a polymer comprising the step of:
  (a) adding bis(2,4-dicumylphenyl)pentaerythritol diphosphite of formula (II)

at least a portion of which is in amorphous form, said amorphous form having an initial melting point between approximately 50° C. and 65° C.

18. The process of claim 17 which further comprises the steps of:
  (a) heating a crystalline form of said bis(2,4-dicumylphenyl)pentaerythritol diphosphite to a temperature to effect melting of said diphosphite;
  (b) adding at least one second additive to said diphosphite and mixing therein to form a melt composite; and
  (c) cooling said melt composite to below to form a solid melt composite, at least a portion of which is amorphous bis(2,4-dicumylphenyl)pentaerythritol diphosphite.

19. The process of claim 18 wherein said step of heating is from 200° C. to 30° C. inclusive.

20. The process of claim 19 wherein said step of cooling comprises at least the step of impinging said melt onto a surface at a temperature of about 50° C. or below.

21. The process of claim 20 wherein said at least one second additive is selected from the group consisting of phosphites and phosphonites.

22. The process of claim 21 wherein said step of adding further comprises adding at least one third additive.

23. The process of claim 22 wherein said at least one third additive is selected from the group consisting of hindered phenolic antioxidants and hindered amine light stabilizers.

24. The process of claim 23 which further comprises the step of adding at least one fourth additive selected from the group consisting of metal deactivators, peroxide scavengers, acid scavengers, basic co-stabilizers, nucleating agents, reinforcing gents, plasticizers, lubricants, emulsifiers, pigments, dyes, optical brighteners, flame-proofing agents, antistatic agents, blowing agents, crosslinking agents, antiblocking agents, slip agents, processing aids and thiosynergists.

25. A process for improving the melt stability of a polymer comprising the step of:-

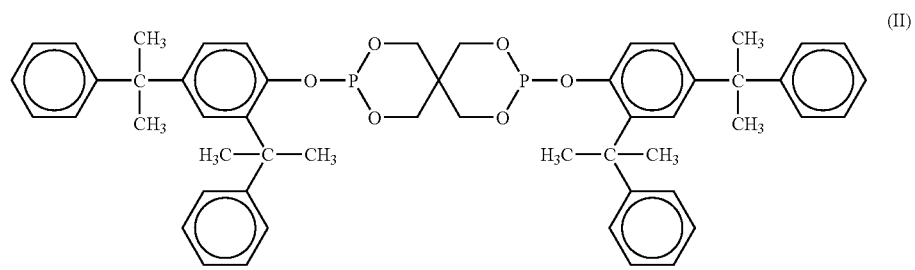

(a) adding a melt blend composite of at least two phosphites one of which is bis(2,4-dicumylphenyl)pentaerythritol diphosphite of formula (II)

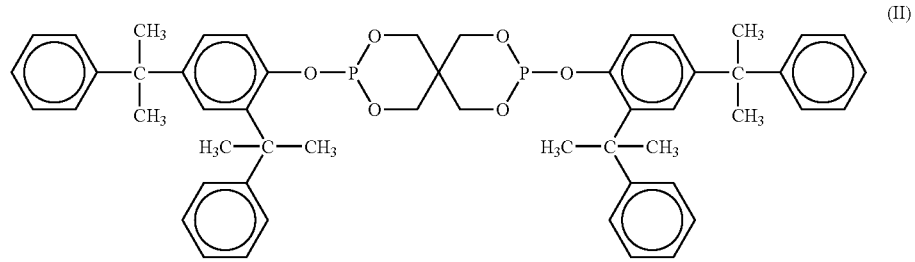

at least a portion of which is in amorphous form, said amorphous form having an initial melting point between approximately 50° C. and 65°C.

dyes, optical brighteners, flame-proofing agents, antistatic agents, blowing agents, crosslinking agents, antiblocking agents, slip agents, processing aids and thiosynergists.

33. A process for forming amorphous bis(arylalkylphenyl) pentaerythritol diphosphite of formula (I)

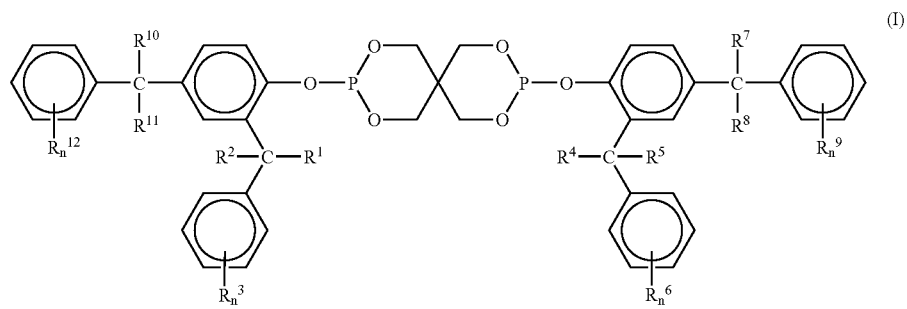

26. The process of claim 25 which further comprises the steps of:
  (a) heating a crystalline form of said bis(2,4-dicumylphenyl)pentaerythritol diphosphite to a temperature to effect melting of said diphosphite;
  (b) adding at least one second additive to said diphosphite and mixing therein to form a melt composite; and
  (c) cooling said melt composite to below to form a solid melt composite, at least a portion of which is amorphous bis(2,4-dicumylphenyl)pentaerythritol diphosphite.

27. The process of claim 26 wherein said step of heating is from 200° C. to 300° C. inclusive.

28. The process of claim 27 wherein said step of cooling comprises at least the step of impinging said melt onto a surface at a temperature of about 50° C. or below.

29. The process of claim 26 wherein said at least one second additive is selected from the group consisting of phosphites and phosphonites.

30. The process of claim 29 wherein said step of adding further comprises adding at least one third additive.

31. The process of claim 30 wherein said at least one third additive is selected from the group consisting of hindered phenolic antioxidants and hindered amine light stabilizers.

32. The process of claim 31 which further comprises the step of adding at least one fourth additive selected from the group consisting of metal deactivators, peroxide scavengers, acid scavengers, basic co-stabilizers, nucleating agents, reinforcing gents, plasticizers, lubricants, emulsifiers, pigments, wherein $R^1$ through $R^{12}$ are independently selected from the group consisting of hydrogen, $C_{1-4}$ alkyls, $C_{1-4}$ alkoxy radicals and further wherein n ranges from 0 to 3, and the substituent is located in a position ortho, meta, or para to the bridging methylene radicals comprising the steps of:
  (a) heating a crystalline form of said diphosphite to a temperature to effect melting of said crystalline form of said diphosphite; and
  (b) cooling said melted diphosphite to form an amorphous solid diphosphite having an initial melting point of between approximately 50° C. and 65° C.

34. The process of claim 33 wherein said step of heating is from 200° C. to 300° C. inclusive.

35. The process of claim 34 wherein said step of cooling comprises at least the step of impinging said melt onto a surface at a temperature of about 50° C. or below.

36. The product of the process of claim 35.

37. The process of claim 33 which further comprises the step of adding at least one second additive to said diphosphite.

38. The process of claim 37 wherein said at least one second additive is selected from the group consisting of phosphites and phosphonites.

39. A process for forming amorphous bis(arylalkylphenyl) pentaerythritol diphosphite of formula (I)

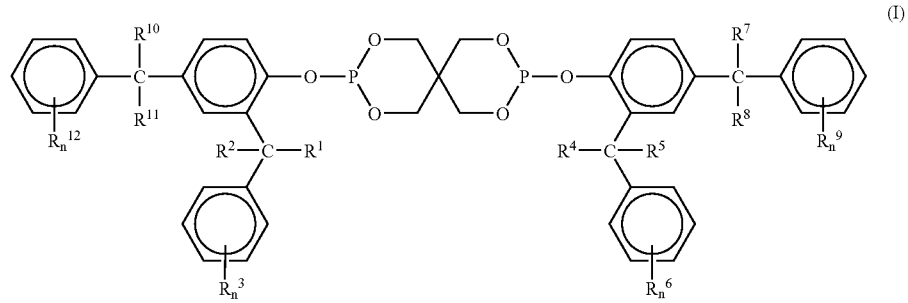

wherein R[1] through R[12] are independently selected from the group consisting of hydrogen, $C_{1-4}$ alkyls, $C_{1-4}$ alkoxy radicals and further wherein n ranges from 0 to 3, and the substituent is located in a position ortho, meta, or para to the bridging methylene radicals comprising the steps of:

(a) heating a crystalline form of said diphosphite to a temperature to effect melting of said diphosphite;

(b) adding at least one second additive to said diphosphite and mixing therein to form a melt composite; and (c) cooling said melt composite to form a solid melt composite, at least a portion of which is amorphous bis(arylalkylphenyl)pentaerythritol diphosphite having an initial melting point between approximately 50° C. and 65° C.

40. The process of claim 39 wherein said step of heating is from 200° C. to 300° C. inclusive.

41. The process of claim 40 wherein said step of cooling comprises at least the step of impinging said melt composite onto a surface at a temperature of about 50° C. or below.

42. The process of claim 40 wherein said at least one second additive is selected from the group consisting of phosphites and phosphonites.

43. A process for improving the melt stability of a polymer comprising the step of:

(a) adding bis(arylalkylphenyl)pentaerythritol diphosphite of formula (I)

substituent is located in a position ortho, meta, or para to the bridging methylene radicals, at least a portion of which is in amorphous form, said amorphous form having an initial melting point between approximately 50° C. and 65° C.

44. The process of claim 43 which further comprises the steps of:

(a) heating a crystalline form of said bis(arylalkylphenyl)pentaerythritol diphosphite to a temperature to effect melting of said diphosphite;

(b) adding at least one second additive to said diphosphite and mixing therein to form a melt composite; and (c) cooling said melt composite to below to form a solid melt composite, at least a portion of which is amorphous bis(arylalkylphenyl)pentaerythritol diphosphite.

45. The process of claim 44 wherein said step of heating is from 200° C. to 300° C. inclusive.

46. The process of claim 45 wherein said step of cooling comprises at least the step of impinging said melt onto a surface at a temperature of about 50° C. or below.

47. The process of claim 46 wherein said at least one second additive is selected from the group consisting of phosphites and phosphonites.

48. A process for improving the melt stability of a polymer comprising the step of:

(a) adding a melt blend composite of at least two phosphites one of which is bis(arylalkylphenyl)pentaerythritol diphosphite of

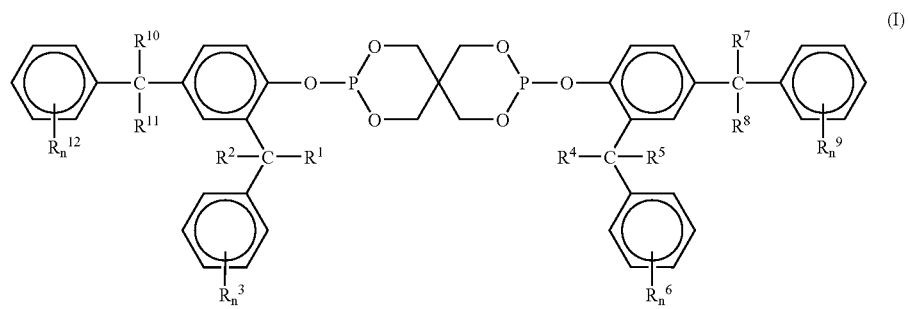

wherein $R_1$ through $R_{12}$ are independently selected from the group consisting of hydrogen, $C_{1-4}$ alkyls, $C_{1-4}$ alkoxy radicals and further wherein n ranges from 0 to 3, and the

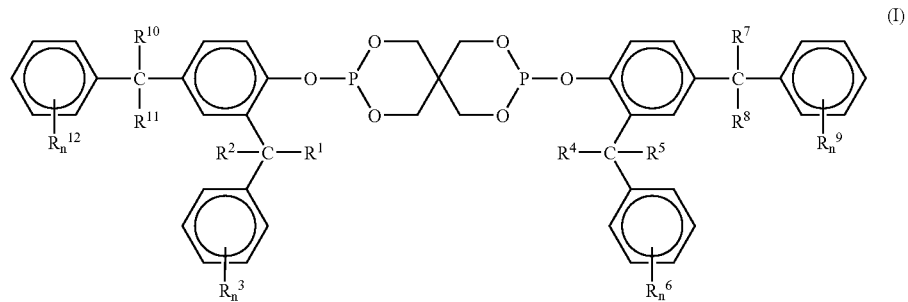

(I)

wherein $R^1$ through $R^{12}$ are independently selected from the group consisting of hydrogen, $C_{1-4}$ alkyls, $C_{1-4}$ alkoxy radicals and further wherein n ranges from 0 to 3, and the substituent is located in a position ortho, meta, or para to the bridging methylene radicals, at least a portion of which is in amorphous form, said amorphous form having an initial melting point between approximately 50° C. and 65° C.

49. The process of claim 48 which further comprises the steps of:
(a) heating a crystalline form of said bis(arylalkylphenyl) pentaerythritol diphosphite to a temperature to effect melting of said diphosphite;
(b) adding at least one second additive to said diphosphite and mixing therein to form a melt composite; and
(c) cooling said melt composite to below to form a solid melt composite, at least a portion of which is amorphous bis(arylalkylphenyl)pentaerythritol diphosphite.

50. The process of claim 49 wherein said step of heating is from 200° C. to 300° C. inclusive.

51. The process of claim 50 wherein said step of cooling comprises at least the step of impinging said melt onto a surface which at a temperature of about 50° C. or below.

52. The process of claim 51 wherein said at least one second additive is selected from the group consisting of phosphites and phosphonites.

* * * * *

UNITED STATES PATENT AND TRADEMARK OFFICE
CERTIFICATE OF CORRECTION

| | |
|---|---|
| PATENT NO. | : 7,176,252 B2 |
| APPLICATION NO. | : 10/778492 |
| DATED | : February 13, 2007 |
| INVENTOR(S) | : Donald R. Stevenson, Satyan Kodali and Carroll W. Larke |

It is certified that error appears in the above-identified patent and that said Letters Patent is hereby corrected as shown below:

Column 32, line 20, by deleting 30° and substituting therefor 300°.

Signed and Sealed this

Tenth Day of July, 2007

JON W. DUDAS
*Director of the United States Patent and Trademark Office*